(12) United States Patent
Bono et al.

(10) Patent No.: US 9,248,228 B2
(45) Date of Patent: Feb. 2, 2016

(54) SUCTION AND IRRIGATION APPARATUS WITH ANTI-CLOGGING CAPABILITY

(71) Applicant: Peter L. Bono, Franklin, MI (US)

(72) Inventors: Peter L. Bono, Franklin, MI (US); James D. Lark, West Bloomfield, MI (US); Anthony J. Ruhala, Almont, MI (US); John S. Scales, Ann Arbor, MI (US)

(73) Assignee: Peter L. Bono, Franklin, MI (US)

( * ) Notice: Subject to any disclaimer, the term of this patent is extended or adjusted under 35 U.S.C. 154(b) by 251 days.

(21) Appl. No.: 13/745,151

(22) Filed: Jan. 18, 2013

(65) Prior Publication Data

US 2014/0207056 A1    Jul. 24, 2014

(51) Int. Cl.
*A61M 3/02* (2006.01)
*A61M 1/00* (2006.01)

(52) U.S. Cl.
CPC ........... *A61M 3/0283* (2013.01); *A61M 1/0045* (2014.02); *A61M 1/0047* (2013.01); *A61M 1/0064* (2013.01)

(58) Field of Classification Search
CPC ............ A61M 1/0058; A61M 1/0062; A61M 1/0064; A61M 3/0283; A61C 17/0202; A61C 17/0208
USPC .......... 604/34, 35, 43, 45, 118, 119, 131, 173
See application file for complete search history.

(56) References Cited

U.S. PATENT DOCUMENTS

| | | | |
|---|---|---|---|
| 3,208,145 A | 9/1965 | Turner | |
| 4,519,385 A * | 5/1985 | Atkinson et al. | 601/161 |
| 4,708,717 A | 11/1987 | Deane et al. | |
| 5,019,054 A | 5/1991 | Clement et al. | |
| 5,061,180 A | 10/1991 | Wiele | |
| 5,123,840 A | 6/1992 | Nates | |
| 5,224,929 A | 7/1993 | Remiszewski | |
| 5,230,704 A | 7/1993 | Moberg et al. | |
| 5,247,966 A | 9/1993 | Stevens et al. | |
| 5,254,083 A | 10/1993 | Gentelia et al. | |
| 5,468,240 A * | 11/1995 | Gentelia et al. | 606/42 |
| 5,496,270 A | 3/1996 | Nettekoven | |
| 5,588,634 A | 12/1996 | Nettekoven | |

(Continued)

FOREIGN PATENT DOCUMENTS

DE    19819432 A1    11/1999
WO    2012/027624 A2    3/2012

OTHER PUBLICATIONS

International Search Report dated May 20, 2014 from PCT/US2014/011791 filed Jan. 16, 2014, 3 pgs.

*Primary Examiner* — Nicholas Lucchesi
*Assistant Examiner* — Melissa A Snyder
(74) *Attorney, Agent, or Firm* — Brooks Kushman P.C.

(57) ABSTRACT

A handheld tool for providing irrigation and/or suction is provided. In certain embodiments, the tool has a single cannula for providing both suction and irrigation, while in others there are separate suction and irrigation cannulas. In some embodiments, flush water is supplied by actuating a flush button which both pinches closed a suction hose and opens a flush hose. If present, the irrigation cannula may be opened by actuating an irrigation button. In certain embodiments, the irrigation and/or flush button may be provided with blade tips to pinch closed the irrigation or flush hoses in cooperation with a blade extending from the tool housing.

29 Claims, 8 Drawing Sheets

(56) References Cited

U.S. PATENT DOCUMENTS

| | | |
|---|---|---|
| 5,630,939 A | 5/1997 | Bulard et al. |
| 6,540,713 B1 | 4/2003 | Cimino |
| 6,932,788 B2 * | 8/2005 | Kamiyama et al. ............. 604/43 |
| 7,025,755 B2 * | 4/2006 | Epstein ........................ 604/500 |
| 7,297,133 B2 | 11/2007 | Nelson et al. |
| 2001/0011162 A1 | 8/2001 | Epstein |
| 2002/0123722 A1 | 9/2002 | French et al. |
| 2003/0130594 A1 | 7/2003 | Hynes et al. |
| 2004/0178129 A1 | 9/2004 | Rizzo |
| 2006/0025794 A1 | 2/2006 | Fanton et al. |
| 2007/0173760 A1 | 7/2007 | Fedenia et al. |
| 2008/0146991 A1 | 6/2008 | Hernandez et al. |
| 2009/0062751 A1 | 3/2009 | Newman, Jr. |
| 2011/0202021 A1 | 8/2011 | Ho |

* cited by examiner

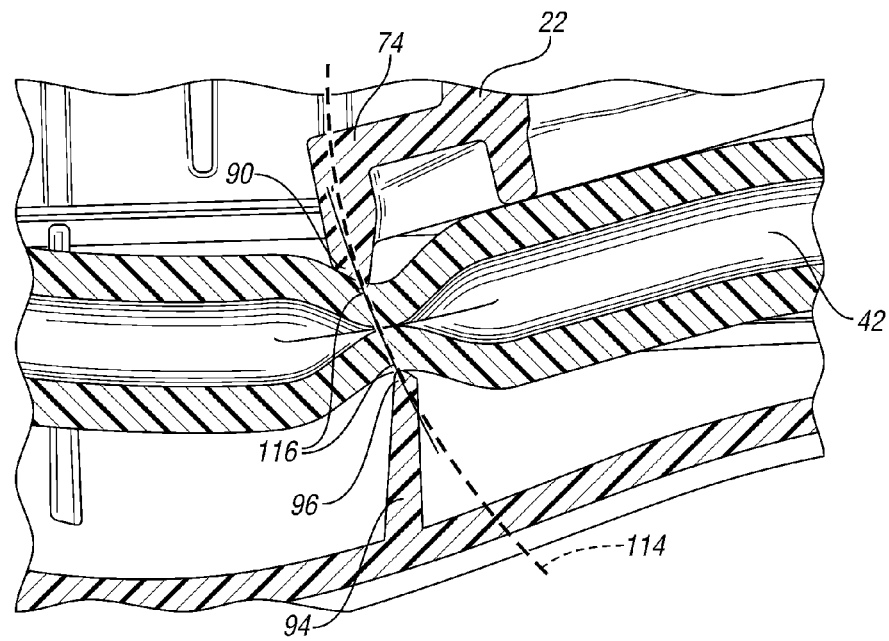
FIG. 15
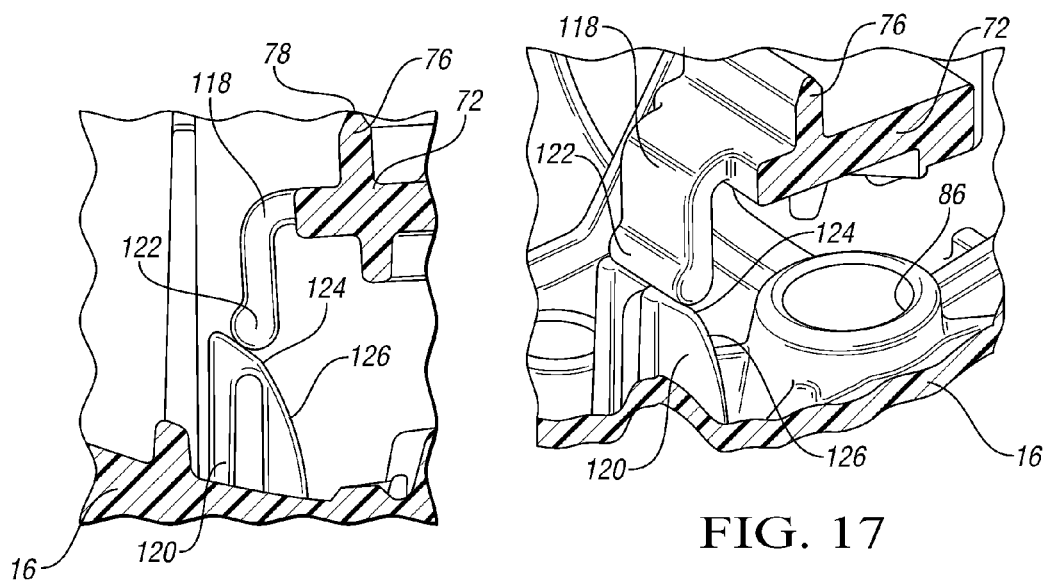
FIG. 16
FIG. 17

US 9,248,228 B2

SUCTION AND IRRIGATION APPARATUS WITH ANTI-CLOGGING CAPABILITY

TECHNICAL FIELD

The present disclosure relates, in at least certain embodiments, to a handheld tool for providing suction and/or irrigation to a wound site or body opening.

BACKGROUND

During medical procedures, for example surgical or dental procedures, it is common for a doctor or other health care professional to provide irrigation fluid to a body site (e.g. a wound or oral cavity). The irrigation fluid may be, for example, water, saline, or another biocompatible fluid. The health care professional may also desire to apply suction to the body site in order to remove fluid or debris. While applying suction, clogging of the suction cannula can occur if a piece of debris enters the cannula and becomes lodged inside. On some occasions, it is beneficial to provide irrigation and suction at the same time. Health care professionals often handle multiple tools at a time, leaving only a single hand to operate each tool. They also conduct procedures with long durations, so tools may be in their hands and in use for extended periods of time.

SUMMARY

In at least one embodiment, a handheld tool for providing irrigation and suction is provided. The tool includes a housing, a suction terminal configured to connect to a source of suction, and an irrigation terminal configured to connect to a source of irrigation fluid. A cannula extends from a distal end of the housing and is configured to deliver fluid or remove fluid or debris from a body site. A suction hose is coupled at one end to the suction terminal and extends to and is coupled to a proximal end of the cannula. A control port hose is in fluid communication with the suction terminal and has one end which terminates at an open port defined in the housing in fluid communication with an outside atmosphere. A flush hose is coupled at one end to the irrigation terminal and at the other end to the suction hose. A flush button is disposed within the housing. The suction hose is configured to be normally open and the flush hose is configured to be normally closed. Actuation of the flush button causes the flush hose to switch to an open position, allowing fluid to flow to the cannula, and pinches the suction hose into a closed position, such that fluid or debris do not travel to the suction source.

In another embodiment, a handheld tool for providing irrigation and suction is provided. The tool includes a housing and a front manifold and a rear manifold disposed within the housing. The rear manifold has a suction terminal configured to connect to a source of suction and an irrigation terminal configured to connect to a source of irrigation fluid. A suction cannula extends from a distal end of the front manifold and is configured to deliver fluid or remove fluid or debris from a body site. A suction hose extends from the suction terminal of the rear manifold to a suction channel in a proximal end of the front manifold, and the suction channel is in fluid communication with the suction cannula. A control port hose extends from the suction terminal of the rear manifold and terminates at an open port defined in the housing, which is in fluid communication with an outside atmosphere. A flush hose extends from the irrigation terminal of the rear manifold to a flush channel in the proximal end of the front manifold and the flush channel terminates in the suction channel. A flush button is disposed within the housing. An irrigation hose extends from the irrigation terminal of the rear manifold through a distal end of the housing and extends adjacent to the suction cannula to form an irrigation cannula. An irrigation button is disposed within the housing. The suction hose is configured to be normally open and the flush hose and irrigation hose are configured to be normally closed. Actuation of the flush button causes the flush hose to switch to an open position, allowing fluid to flow to the suction cannula, and pinches the suction hose into a closed position, such that fluid or debris do not travel to the suction source. Actuation of the irrigation button causes the irrigation hose to switch to an open position, allowing fluid to flow to the irrigation cannula.

In another embodiment, a handheld tool for providing irrigation and suction is provided. The tool includes a housing and a front manifold and a rear manifold disposed within the housing. The rear manifold has a suction terminal configured to connect to a source of suction and an irrigation terminal configured to connect to a source of irrigation fluid. A cannula extends from a distal end of the front manifold and is configured to deliver fluid or remove fluid or debris from a body site. A suction hose extends from the suction terminal of the rear manifold to a suction channel in a proximal end of the front manifold, the suction channel in fluid communication with the cannula. A control port hose extends from the suction terminal of the rear manifold and terminates at an open port defined in the housing, which is in fluid communication with an outside atmosphere. A flush hose extends from the irrigation terminal of the rear manifold to a flush channel in the proximal end of the front manifold and the flush channel terminates in the suction channel. A flush button is disposed within the housing. The suction hose is configured to be normally open and the flush hose is configured to be normally closed. Actuation of the flush button causes the flush hose to switch to an open position, allowing fluid to flow to the cannula, and pinches the suction hose into a closed position, such that fluid or debris do not travel to the suction source.

BRIEF DESCRIPTION OF THE DRAWINGS

FIG. 15 is an enlarged side section view of an embodiment of the suction valve with the flush button actuated and the suction hose pinched closed;

FIG. 16 is a cutaway side view of an embodiment with the flush button having a snapover member and the housing having a snap projection;

FIG. 17 is a cutaway perspective view of the embodiment of FIG. 16;

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention. Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred.

Figure 1:
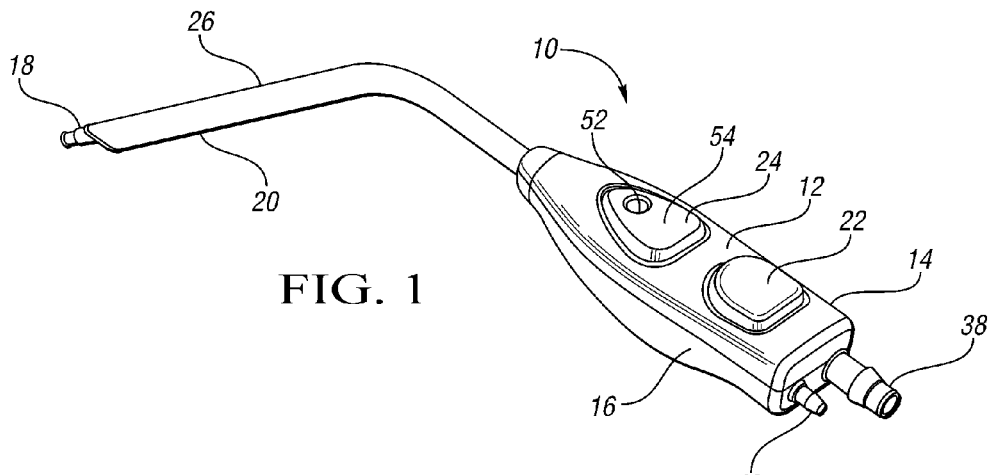
FIG. 1 is a perspective view of an embodiment having dual cannulas.
Figure 2:
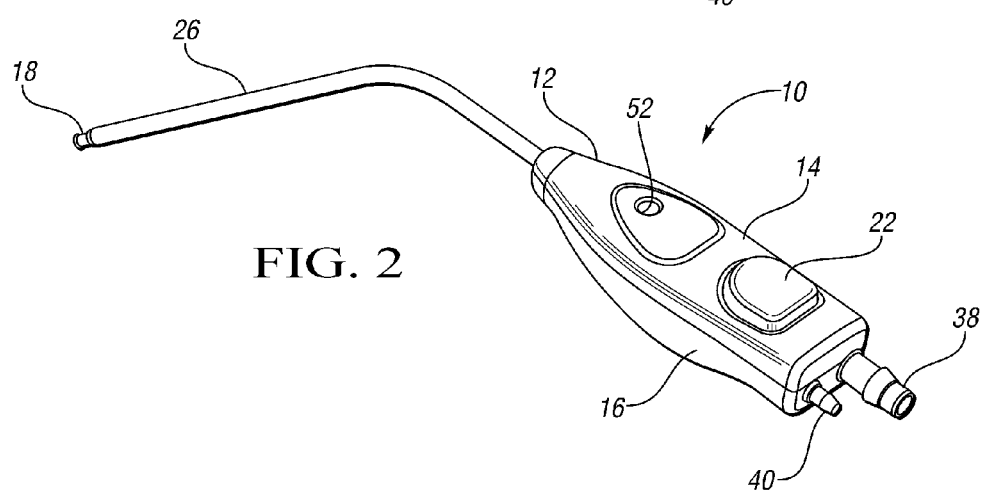
FIG. 2 is a perspective view of an embodiment having a single cannula.

With respect to FIGS. 1 and 2, a handheld tool 10 for providing irrigation and suction is shown. The tool 10 has a housing 12, which may be formed from multiple pieces and is shown having a top half 14 and a bottom half 16. In some embodiments, such as shown in FIG. 1, the tool 10 has a dual lumen/cannula configuration, providing a suction cannula 18 and an irrigation cannula 20 separately. In other embodiments, such as shown in FIG. 2, the tool 10 has a single lumen/cannula 18 that provides both suction and irrigation. Dual cannula embodiments may have two buttons, a flush button 22 and an irrigation button 24, while single cannula embodiments may have a single button, the flush button 22. As shown in the Figures, the buttons may be arranged axially with the flush button 22 in the rear and the irrigation button 24 (when present) in the front. However, the flush button 22 and irrigation button 24 can be arranged in any manner, for example with the flush button 22 in the front and irrigation in the rear, side by side, or other arrangement.

In embodiments having dual cannulas, a sleeve 26 may be provided to hold the two cannulas together. The sleeve 26 may be made of any material suitable for contact with the body and bodily fluids and may be a heat shrinkable material to ensure that the suction cannula 18 and irrigation cannula 20 are held firmly together. The sleeve 26 may also have an outer matte finish in order to prevent reflection of light off of the cannulas. A sleeve 26 may also be included in embodiments having a single cannula 18 in order to prevent light reflection.

Figure 3:
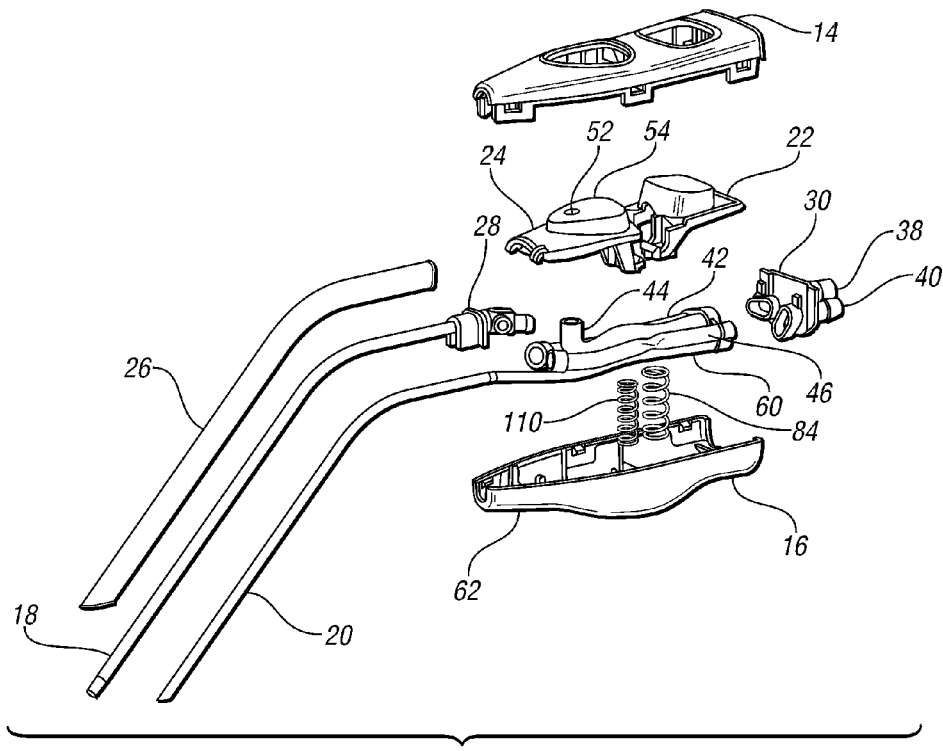
FIG. 3 is an exploded view of an embodiment having dual cannulas.
Figure 4:
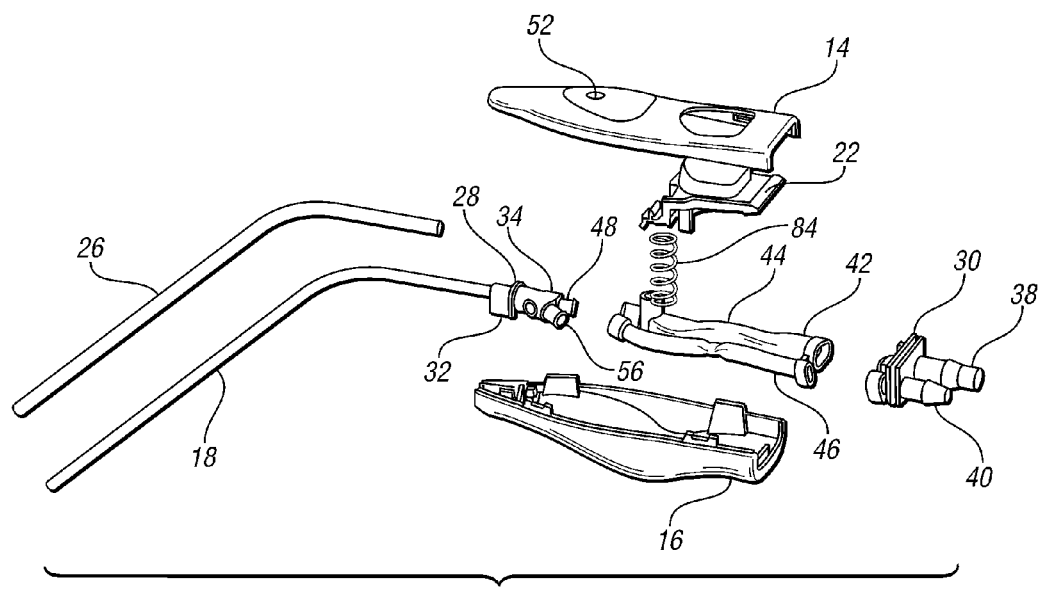
FIG. 4 is an exploded view of an embodiment having a single cannula.

With respect to FIGS. 3 and 4, in at least some embodiments the housing 12 for both the dual cannula embodiments and single cannula embodiments include a front manifold 28 and a rear manifold 30, with "front" referring to the end of the housing 12 having the cannula(s) extending therefrom and "rear" referring to the end opposite the cannula 18(s). As used herein, the terms "distal" and "proximal" have the same orientation, respectively, as front and rear. The front manifold 28 has a distal end 32 and a proximal end 34, with the suction cannula 18 being received in a cannula channel 36 in the distal end 32 of the front manifold 28. The proximal end 34 of the front manifold 28 has a split, or "Y" configuration, having two channels, which will be described in further detail below. The rear manifold 30 has two terminals, a suction terminal 38 configured to be attached to a source of suction (e.g. vacuum) and an irrigation terminal 40 configured to be attached to a source of irrigation fluid (e.g. water or saline).

Figure 5:
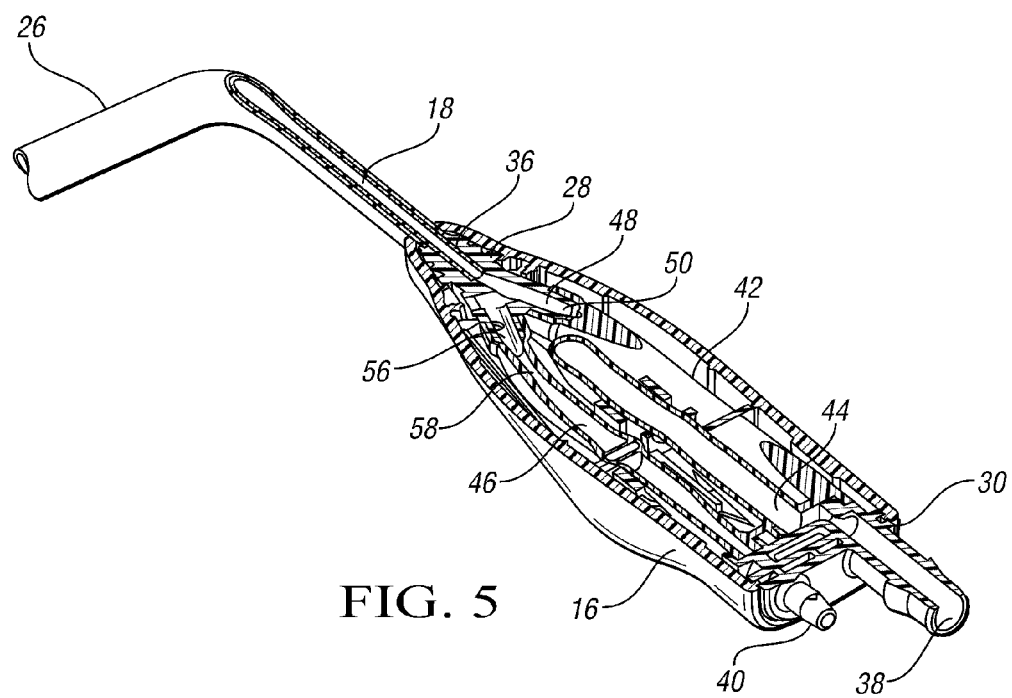
FIG. 5 is a sectioned perspective view of an embodiment having dual cannulas.

Referring to FIGS. 3-5, within the housing 12, for both the dual and single cannula embodiments, three hoses or other such conduits may be utilized: a suction hose 42, a control port hose 44, and a flush hose 46. The suction hose 42 attaches to the suction terminal 38 of the rear manifold 30 and extends to the proximal end 34 of the front manifold 28, where it attaches to a suction channel 48, which is one of the two channels in the split proximal end 34 of the front manifold 28. Accordingly, a continuous path is formed from the cannula 18, through the cannula channel 36 and the suction channel 48 of the front manifold 28, through the suction hose 42, to the suction terminal 38 of the rear manifold 30, and from there through a conduit (not shown) to the source of suction. This path may be referred to as the suction path 50, and is common to both dual and single cannula embodiments.

A control port hose 44, such as shown in FIGS. 3-5, also attaches to the suction terminal 38 of the rear manifold 30, and extends through the housing 12 and terminates at an open port 52 defined in the housing 12 such that it is in fluid communication with the outside atmosphere. In this respect, "in the housing" refers to the housing 12 itself and any buttons or other components disposed therein or protruding therefrom. In at least one embodiment having a dual cannula, the open port 52 is located on a top surface 54 of the irrigation button 24. The only requirement for the open port 52 is that it provides an opening to an outside atmosphere. Since the control port hose 44 and the suction hose 42 both attach to the suction terminal 38 of the rear manifold 30, they may optionally merge to form a common hose at one end where they attach to the suction terminal 38. Alternatively, the two hoses may remain separate and the suction terminal 38 may connect to each individually and have a common channel leading to the source of suction. In one embodiment, a check valve (described in more detail below) is provided in the control port hose 44 to allow air to travel into the suction path but prevent any liquid from exiting through the open port 52.

As can be seen from FIGS. 1-4, the control port hose 44 and open port 52, combined with the suction hose 42 and source of suction, facilitate an easy and single-handed suction operation by a user of the tool 10. In practice, the source of suction is maintained in an "on" state such that suction is constantly being applied to the suction hose 42 and the control port hose 44. However, due to the open port 52, there is very little or no actual suction applied at the tip of the suction or single cannula 18 when inserted into a patient's body because air is preferentially pulled though the open port 52. When the user of the tool 10 desires to apply suction through the suction path 50, he/she covers the open port 52, generally with a single finger, thereby obstructing the control port hose 44 from the atmosphere and causing suction to be applied through the cannula 18 to remove fluid and/or debris.

Figure 6:
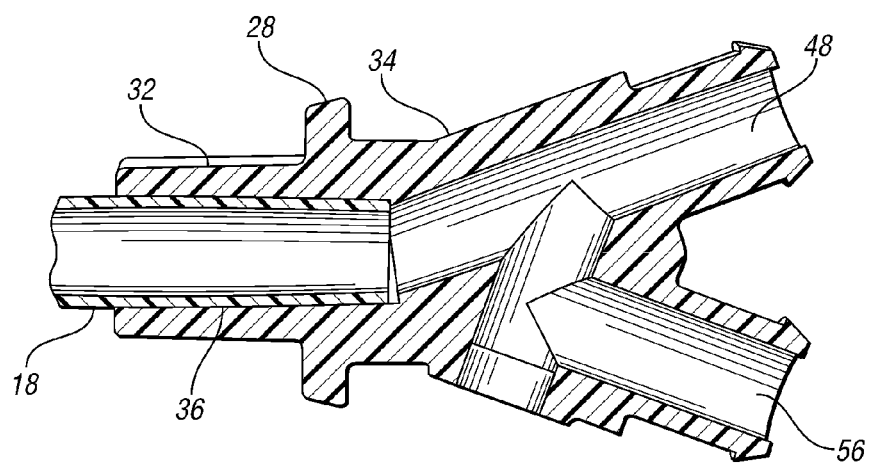
FIG. 6 is a cross-section view of an embodiment of a front manifold.

Again common to both dual and single cannula embodiments, a flush hose 46 is provided that extends from the irrigation terminal 40 of the rear manifold 30 to the proximal end 34 of the front manifold 28, where it attaches to a flush channel 56, which is the other of the two channels in the split proximal end 34 of the front manifold 28. As shown in FIGS. 5 and 6, the flush channel 56 extends into and terminates in the suction channel 48 of the front manifold 28. In at least one embodiment, the flush channel 56 extends into and terminates in the suction channel 48 at a reentrant or rearward angle such that the flush liquid enters the suction channel 48 at least partially in the direction of the suction path 50 (i.e. traveling towards the suction source). The reentrant or rearward angle of the termination of the flush channel 56 ensures that debris or fluid traveling through the suction path 50 cannot travel into or through the flush channel 56, where it could possibly become clogged.

Accordingly, a continuous path is formed from the irrigation source (not shown), to the irrigation terminal 40 of the rear manifold 30, through the flush hose 46, through the flush channel 56, a portion of the suction channel 48, and then the cannula channel 36 of the front manifold 28, and then though the suction or single cannula 18. This path may be referred to as the flush path 58, and is common to both dual and single cannula embodiments.

As shown in FIG. 3, the dual cannula embodiments have an additional hose, the irrigation hose 60. In at least one embodiment, the irrigation hose 60 extends from the irrigation terminal 40 of the rear manifold 30 and extends through a distal end 62 of the housing 12 and continues to extend adjacent to the suction cannula 18, thereby forming an irrigation cannula 20. In these embodiments, the portion of the irrigation hose 60 extending outside of the housing 12 and forming the irrigation cannula 20 is referred to as the cannula portion of the irrigation hose 60. The cannula portion may be held to the suction cannula 18 by the sleeve 26, or may be otherwise affixed through mechanical attachment or adhesives. In other embodiments, the irrigation hose 60 may terminate inside the housing 12, for example in an irrigation channel 64 (not shown) in the front manifold 28 or in a separate channel, and a separate irrigation cannula 20 may extend alongside the suction cannula 18. In these embodiments, the cannulas may be fused or otherwise be formed from a single piece, or they may be separate and held together as described above (e.g. via the sleeve 26 or mechanically/chemically attached).

Similar to the suction hose 42 and the control port hose 44 both connecting to the suction terminal 38, both the flush hose 46 and the irrigation hose 60 connect to the irrigation terminal 40. As with the suction and control port hoses, the flush and irrigation hoses may optionally merge to form a common hose at one end where they attach to the irrigation terminal 40. Alternatively, the two hoses may remain separate and the irrigation terminal 40 may connect to each individually and have a common channel leading to the source of irrigation. A continuous path is formed from the irrigation source (not shown), to the irrigation terminal 40 of the rear manifold 30, through the irrigation hose 60, and out either the cannula portion of the irrigation hose 60 or a separate irrigation cannula 20. This path may be referred to as the irrigation path 66, and is only present in dual cannula embodiments.

While the embodiments illustrated include front and rear manifolds 28, 30, in other embodiments the hoses may connect directly to the cannula(s) and/or may merge with one another directly rather than connect to a manifold. For example, the flush hose 46, instead of connecting to the suction hose 42 through the front manifold 28, may merge with the suction hose directly to complete the flush path 58. In addition, rather than connect to the cannula 18 through the front manifold 28, the suction hose 42 may be coupled directly to the cannula 18. In some embodiments, the rear manifold 30 may be eliminated in a similar manner. For example, at least one of the suction hose 42, control port hose 44, and flush hose 46 may be coupled directly to the source of suction or irrigation rather than through the rear manifold 30. In another embodiment, the control port hose 44 may split off from the suction hose 42 such that they share a common portion connected to and in fluid communication with the rear manifold 30 (or direct connection to the source of suction, as just described).

Figure 7:
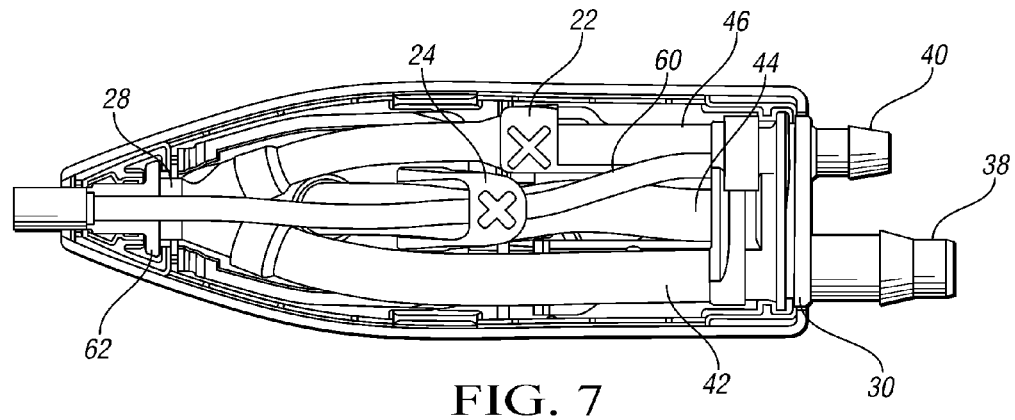
FIG. 7 is a cutaway bottom view of an embodiment having dual cannulas.

With respect to FIGS. 5-15, the operation of the tool 10 will be described. As explained above, the suction hose 42, control port hose 44, and flush hose 46, as well as the front manifold 28 and rear manifold 30 are the same or similar in both dual and single cannula embodiments. In at least one embodiment, the suction hose 42 and the control port hose 44 are open when no buttons are being actuated, which herein will be described as "normally open," and the flush hose 46 is closed when no buttons are being actuated, which herein will be described as "normally closed." Therefore, with the buttons not actuated (such as shown in FIG. 7), suction is applied through the suction hose 42 and the control port hose 44 and no fluid travels through the flush hose 46 (however, without covering the open port 52, negligible suction is applied through the suction cannula 18, as described above). This state could be referred to as the rest state or inactive state. The configuration and operation of the buttons and how they open and close the hoses will be discussed in greater detail following the description of the buttons' effects.

The flush button 22 operates in the same way for both the dual and single cannula embodiments, however it serves a different purpose in each. Since the single cannula embodiments do not have a separate irrigation hose 60 and irrigation cannula 20, the flush button 22 and flush path 58 operate to provide irrigation through the suction cannula 18 (i.e. there can be no simultaneous irrigation and suction). As described above, the flush hose 46 is normally closed and the suction hose 42 is normally open. When the user of a single cannula tool 10 wishes to provide irrigation, the flush button 22 is actuated. As shown in FIGS. 8-11, actuation of the flush button 22 causes the flush hose 46 to open and the suction hose 42 to close. Therefore, fluid flows through the flush path 58 and out through the suction cannula 18. In at least one embodiment, described previously and shown in FIG. 6, the flush channel 56 extends into and terminates in the suction channel 48 at a rearward angle. This means that upon actuation of the flush button 22, a small amount of irrigation fluid may be suctioned off through the suction hose 42 if the suction hose 42 is not closed before the irrigation fluid arrives. However, once the suction hose 42 is closed, the only outlet of the irrigation fluid is through the suction cannula 18 and the irrigation fluid will exit therefrom.

Figure 12:
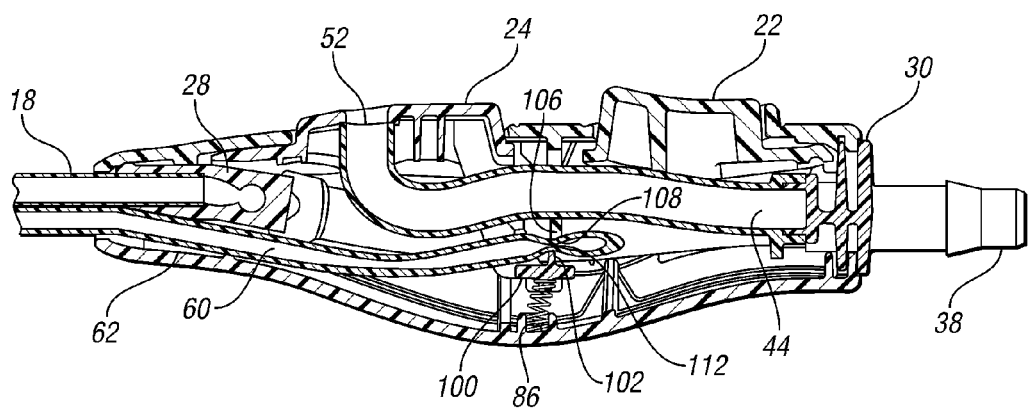
FIG. 12 is a side section view of an embodiment having dual cannulas with both irrigation and flush buttons un-actuated and the control port hose open and the irrigation hose pinched closed.
Figure 13:
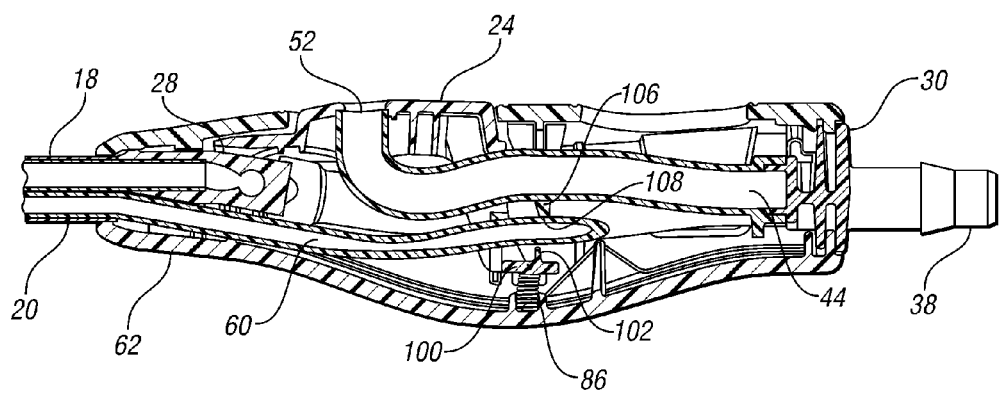
FIG. 13 is a side section view of an embodiment having dual cannulas with the flush button removed for clarity and showing the irrigation button actuated and the irrigation hose open.

In embodiments having dual cannulas, the irrigation hose 60 is also normally closed, and therefore the same result occurs when the tool 10 is in the rest state: the suction hose 42 and control port hose 44 are open and the flush hose 46 and irrigation hose 60 are closed. As shown in FIGS. 12-13, if the user wants to initiate irrigation, the irrigation button 24 is pushed and the irrigation hose 60 is opened, thereby allowing fluid to travel through the irrigation path 66 and out of the irrigation cannula 20. Since the irrigation hose 60 is independent of the suction hose 42 and suction cannula 18, the dual cannula embodiments allow for simultaneous irrigation and suction by actuating the irrigation button 24 and covering the open port 52 connected to the control port hose 44. In embodiments where the open port 52 is located on the top surface 54 of the irrigation button 24, simultaneous irrigation and suction can be accomplished with a single finger by pushing down on the irrigation button 24 while also covering the open port 52, thereby making the process extremely easy for the user and freeing up their other hand/fingers for other tasks.

In embodiments having dual cannulas, and therefore a separate irrigation hose 60, the purpose of the flush hose 46 is to flush out clogs that may occur in the suction cannula 18, the cannula channel 36, or the suction channel 48. Actuation of the flush button 22 in single cannula embodiments does, of course, also flush out clogs in the same manner when providing irrigation fluid. It is possible to provide a "partial pressure flush" in either of the embodiments by only partially actuating the flush button 22. As will be described more fully below, this will result in the flush hose 46 being partially opened and the suction hose 42 being partially closed. Therefore, some flush fluid may escape through the partially open flush hose 46, but the reduced flush fluid will still be sufficient to flush a small clog in the cannula 18. This partial pressure flush may be useful when there is a small clog and it is not desirable to supply large volumes of flush fluid. For larger clogs, or when larger flush volumes are acceptable, the user may fully actuate the flush button 22, thereby fully opening the flush hose 46 and fully closing the suction hose 42. If there is a large clog, a full actuation will cause pressure to build up behind the clog due to the fully closed suction hose 42, helping to flush the clog out of the suction cannula 18.

Figure 8:
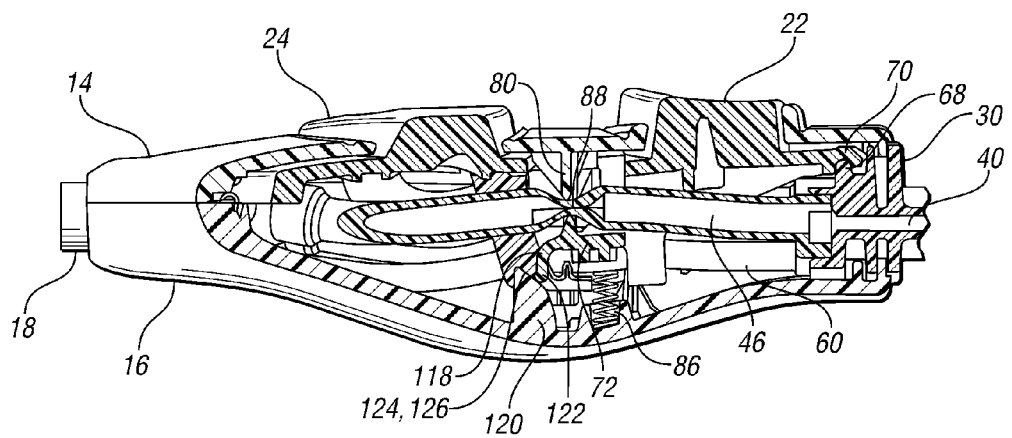
FIG. 8 is a side section view of an embodiment having dual cannulas with both irrigation and flush buttons un-actuated and the flush hose pinched closed.

The operation of the flush button 22 and irrigation button 24 (when present) will now be described with respect to FIGS. 3-4 and 7-15. In at least one embodiment, the flush button 22 and irrigation button 24 are hinge-mounted in the housing 12. The hinge mounting may comprise a hinge male portion 68 on either the housing 12 or one of the front or rear manifolds and a hinge female portion 70 on the flush button 22 and the irrigation button 24, for example as shown in FIG. 8. However, any configuration known in the art for allowing for a hinged connection between the housing 12 or components therein may be used. In addition, in other embodiments (not shown) one or both of the flush button 22 and irrigation button 24 may be mounted in the housing 12 without a hinged connection. In at least one embodiment, the flush button and/or irrigation button may be vertical push buttons, that is they move linearly up and down (or side to side if the button is horizontal). Examples of other potential button mountings include side-to-side rockers, fore-aft rockers, and triggers.

Figure 9:
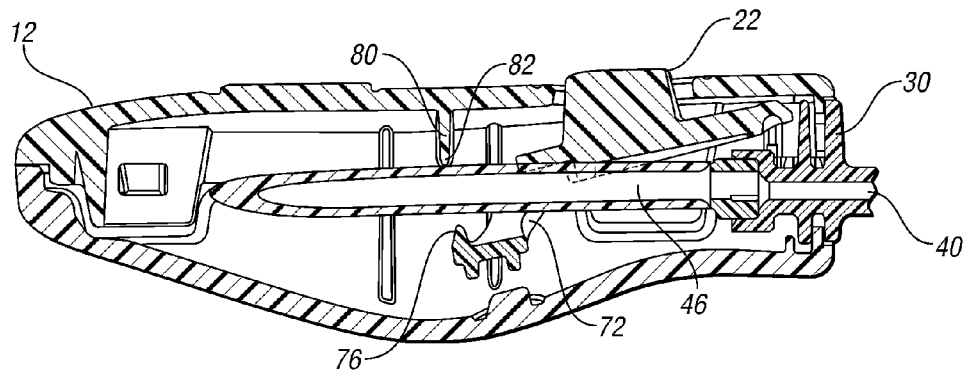
FIG. 9 is a side section view of an embodiment having a single cannula with the flush button actuated and the flush hose open.

In at least one embodiment, the flush button 22 has two projections, a first projection 72 configured to contact and selectably open and close the flush hose 46 and a second projection 74 configured to contact and selectably open and close the suction hose 42. In at least one embodiment, the first projection 72 extends downward from a body of the flush button 22 and underneath the flush hose 46, for example as seen in FIGS. 8-9. The first projection 72 has a blade tip 76 extending transverse to a longitudinal axis of the flush hose 46 and is configured to engage the flush hose 46 transversely across its longitudinal axis. In at least one embodiment, the blade tip 76 has a side profile in cross-section that tapers to a rounded edge 78. The housing 12 has a flush hose blade 80 extending from a side wall thereof or from a component situated within the housing 12. The flush hose blade 80 also has a blade tip 82 extending transverse to the longitudinal axis of the flush hose 46 and configured to engage the flush hose 46 transversely across its longitudinal axis. In at least one embodiment, the flush hose blade 80 engages the flush hose 46 from above, for example as seen in FIGS. 8-9. However, in embodiments where the flush button 22 is located, for example, on the bottom of the tool, the relative locations of the first projection 72 and flush hose blade 80 may be reversed, such that the first projection 72 is disposed above the flush hose 46 and the flush hose blade 80 engages the flush hose 46 from below. In other embodiments, the first projection 72 and flush hose blade 80 may engage the flush hose 46 from the sides, for example if the hinge was mounted on the side of the housing 12 or if the button was a side-to-side rocker.

A spring 84 is disposed within the housing 12 and extends between the flush button 22 first projection 72 and a side wall of the housing 12, or a component therein. In at least one embodiment, there is an annular well 86 formed in the housing 12 for receiving the spring 84 and holding it in place. The flush button 22 first projection 72 may have an annular well 86, also, or the spring 84 may be attached to the first projection 72 in any suitable manner known in the art. In at least one embodiment, the spring 84 is configured such that it biases the first projection 72 upward when the flush button 22 is not actuated (i.e. at rest), causing the blade tip 76 of the flush button 22 to pinch the flush hose 46 against the blade tip 82 of the flush hose blade 80 extending from the housing 12 and close the flush hose 46, as shown in FIG. 8. When the flush button 22 is actuated by a user pushing it downward, the button and its first projection 72 travel in a downward arc, due to the hinge mounting, thereby overcoming the spring 84 bias and causing the flush hose 46 to be opened, as shown in FIG. 9. The first projection 72 blade tip 76 and the flush hose blade 80 therefore cooperate, along with the spring 84, to form a flush valve 88 for opening and closing the flush hose 46.

Figure 10:
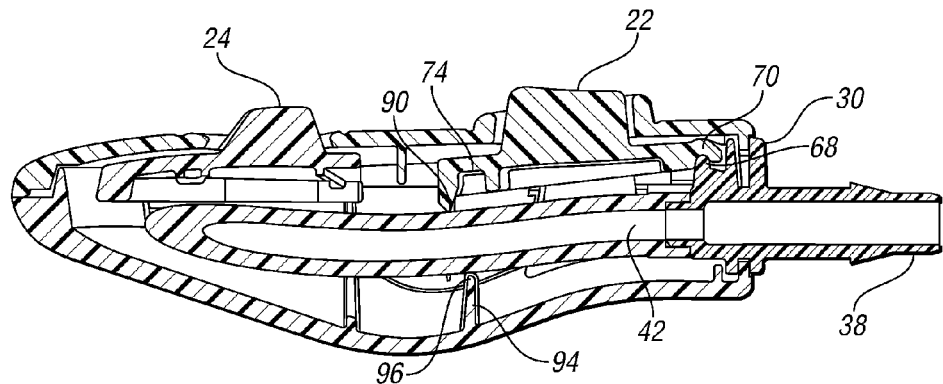
FIG. 10 is a side section view of an embodiment having dual cannulas with both irrigation and flush buttons un-actuated and the suction hose open.
Figure 11:
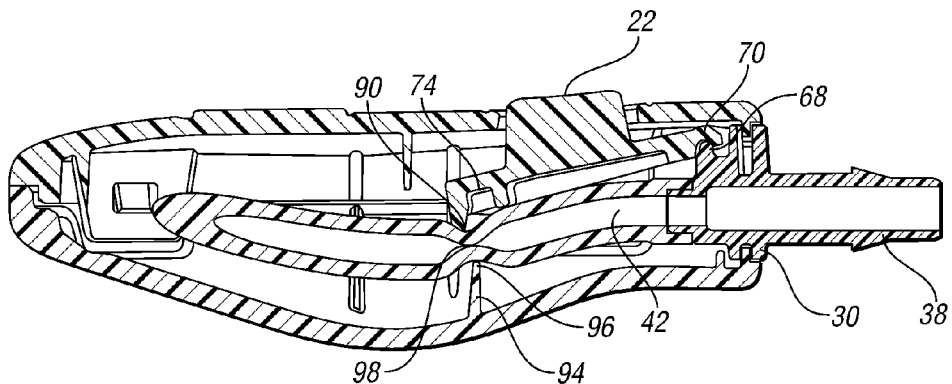
FIG. 11 is a side section view of an embodiment having a single cannula with the flush button actuated and the suction hose pinched closed.

In at least one embodiment, the second projection 74 of the flush button 22 extends downward from the body of the flush button 22 but is above the suction hose 42, for example as shown in FIGS. 10-11. The second projection 74 has a blade tip 90 extending transverse to a longitudinal axis of the suction hose 42 and is configured to engage the suction hose 42 transversely across its longitudinal axis. In at least one embodiment, the blade tip 90 has a side profile in cross-section that tapers to a rounded edge 92. The housing 12 has a suction hose blade 94 extending from a side wall thereof or from a component situated within the housing 12. The suction hose blade 94 also has a blade tip 96 extending transverse to the longitudinal axis of the suction hose 42 and configured to engage the suction hose 42 transversely across its longitudinal axis. In at least one embodiment, the suction hose blade 94 engages the suction hose 42 from below, for example as seen in FIGS. 10-11. However, in embodiments where the flush button 22 is located, for example, on the bottom of the tool, the relative locations of the second projection 74 and suction hose blade 94 may be reversed, such that the second projection 74 is disposed below the suction hose 42 and the suction hose blade 94 engages the suction hose 42 from above. In other embodiments, the second projection 74 and suction hose blade 94 may engage the suction hose 42 from the sides, for example if the hinge was mounted on the side of the housing 12 or if the button was a side-to-side rocker.

No spring is necessary for the closing of the suction hose 42 by the second projection 74. When the flush button 22 is actuated by a user pushing it downward, the button and its second projection 74 travel in a downward arc, due to the hinge mounting. This causes the blade tip 90 of the second projection 74 to pinch the suction hose 42 against the suction hose blade tip 96, thereby closing the suction hose 42, as shown in FIG. 11. The second projection blade tip 90 and the suction hose blade 94 therefore cooperate to form a suction valve 98 for opening and closing the suction hose 42.

The irrigation button 24 has a third projection 100 configured to contact and selectably open and close the irrigation hose 60 in dual cannula embodiments. In at least one embodiment, the third projection 100 extends downward from a body of the irrigation button 24 and underneath the irrigation hose 60, for example as seen in FIGS. 12-13. The third projection 100 has a blade tip 102 extending transverse to a longitudinal axis of the irrigation hose 60 and is configured to engage the irrigation hose 60 transversely across its longitudinal axis. In at least one embodiment, the blade tip 102 has a side profile in cross-section that tapers to a rounded edge 104. The housing 12 has an irrigation hose blade 106 extending from a side wall thereof or from a component situated within the housing 12. The irrigation hose blade 106 also has a blade tip 108 extending transverse to the longitudinal axis of the irrigation hose 60 and configured to engage the irrigation hose 60 transversely across its longitudinal axis. In at least one embodiment, the irrigation hose blade 106 engages the irrigation hose 60 from above, for example as seen in FIGS. 12-13. However, in embodiments where the irrigation button 24 is located, for example, on the bottom of the tool, the relative locations of the third projection 100 and irrigation hose blade 106 may be reversed, such that the third projection 100 is disposed above the irrigation hose 60 and the irrigation hose blade 106 engages the irrigation hose 60 from below. In other embodiments, the third projection 100 and irrigation hose blade 106 may engage the irrigation hose 60 from the sides, for example if the hinge was mounted on the side of the housing 12 or if the button was a side-to-side rocker.

A spring 110 is disposed within the housing 12 and extends between the irrigation button 24 projection and a side wall of the housing 12, or a component therein. In at least one embodiment, there is an annular well 86 formed in the housing 12 for receiving the spring 110 and holding it in place. The irrigation button 24 projection may have an annular well 86, also, or the spring 110 may be attached to the third projection 100 in any suitable manner known in the art. In at least one embodiment, the spring 110 is configured such that it biases the third projection 100 upward when the irrigation button 24 is not actuated (i.e. at rest), causing the blade tip 102 of the irrigation button 24 to pinch the irrigation hose 60 against the blade tip 108 of the irrigation hose blade 106 extending from the housing 12 and close the irrigation hose 60, as shown in FIG. 12. When the irrigation button 24 is actuated by a user pushing it downward, the button and its projection travel in a downward arc, due to the hinge mounting, thereby overcoming the spring 110 bias and causing the irrigation hose 60 to be opened, as shown in FIG. 13. The irrigation button 24 blade tip 102 and the irrigation hose blade 106 therefore cooperate, along with the spring 110, to form an irrigation valve 112 for opening and closing the irrigation hose 60.

Figure 14:
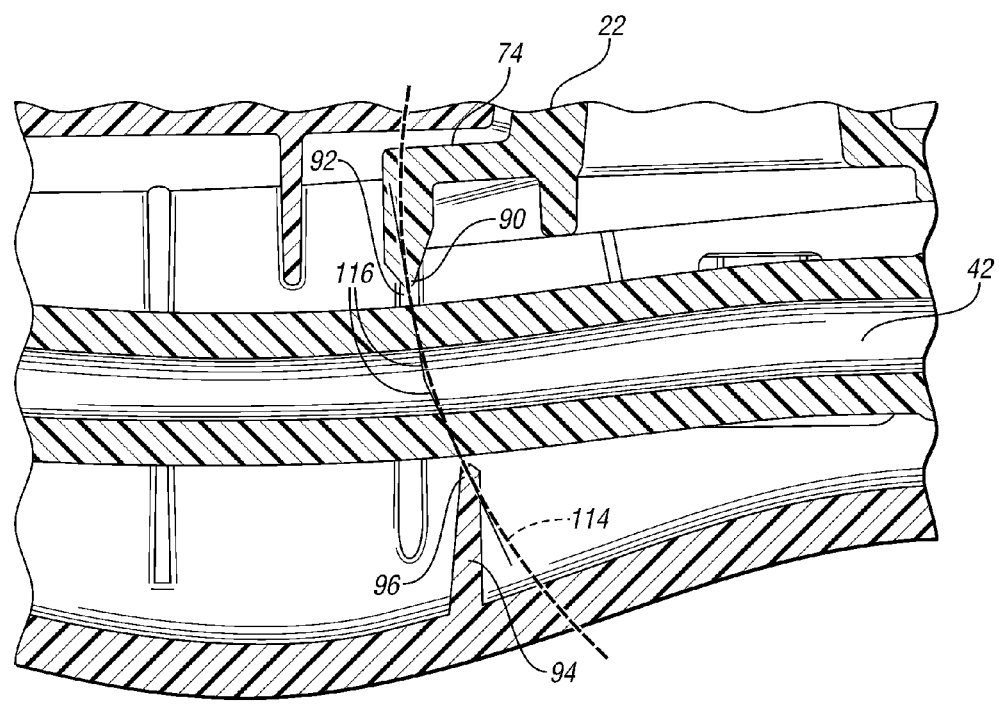
FIG. 14 is an enlarged side section view of an embodiment of the suction valve with the flush button un-actuated and the suction hose open.

With respect to FIGS. 14 and 15, enlarged views of at least one embodiment of the valves in an open and closed position are shown, using the suction valve 98 as an example. However, embodiments of the irrigation valve 112 and flush valve 88 may operate in a similar manner. The arc path 114 of the flush button 22 is shown as a dotted line and the solid lines 116 bisect the blade tips 90, 96 of the second projection 74 and the suction hose blade 94. In at least one embodiment, the blade tips 90, 96 are slightly offset when in a closed position in order to compensate for the circular arc motion of the hinged buttons. When the suction valve 98 is open, such as shown in FIG. 14, the bisecting lines are not collinear, but rather intersect at an angle. To most effectively close the hose, the blade tips 90, 96 may be configured such that the bisecting lines intersect at a very high angle or are substantially collinear when the hose is completely closed, such as shown in FIG. 15. In at least one embodiment, the bisecting lines intersect at an angle from 170 to 190 degrees.

In certain embodiments, the hose may be completely closed when the blade tips 90, 96 are separated by a distance substantially equal to about two times the hose wall thickness, such as shown in FIG. 15. In other embodiments, additional compression may be necessary to fully close the hose. In one embodiment, the blade tips 90, 96 may be separated by about 1.5 times the hose wall thickness when in a fully closed position. In another embodiment, the blade tips 90, 96 may be separated by about a single hose wall thickness when in a fully closed position.

According to at least one embodiment, the suction and irrigation tool 10 is configured and sized to be held by a user with only a single hand and any and all of the buttons are operated with only a single finger, for example a thumb. In addition, all of the hoses, springs, and button projections are completely disposed within the housing 12 and the buttons and the manifolds are at least partially disposed within the housing 12.

In dual cannula embodiments, the user can provide suction by covering the open port 52 (located, for example, on the irrigation button 24) with a finger. To provide irrigation, the user merely pushes down on the irrigation button 24 with the same finger. If simultaneous suction and irrigation is desired, the user may keep the open port 52 covered; otherwise the user may simply slide the finger off the open port 52 and actuate the irrigation button 24. To provide flush liquid (or to irrigate, in single cannula embodiments), the user merely has to slide the finger a short distance to the flush button 22 and press down. Accordingly, all three functions are easily completed with a single finger and without the user having to adjust his/her grip. Similarly, in single cannula embodiments, the user can provide suction by covering the open port 52, located in the housing 12 (for example in front of or behind the flush button 22), with a finger. To provide irrigation (and also flush), the user merely slides the finger to the flush button 22 and presses down.

To provide embodiments having a handheld size and single finger operation, with all hoses, springs, and button projections located within the housing 12, substantial hurdles must be overcome. Typical suction and irrigation tools are sized and configured such that they are difficult to operate with a single hand, and even more difficult to operate with a single finger. The housings are either large or they are split into multiple pieces to accommodate the internal valves. The reason for this is that in order to open and close the hoses or channels, the valves must utilize some form of mechanical advantage, for example an inclined plane or a cam. Often, these tools use valve stems having ends with relatively large radii in order to pinch a hose against a side wall or other curved surface. These valves, while perhaps effective, take up valuable space within the housing or must be external to the housing.

To accomplish the small, handheld housing 12 and single finger operation, at least some embodiments are provided with valves having two opposing blade tips, as described above. Using blades tips with relatively small radii allows the pinching efficiency of the valve to be maximized, thereby allowing a reduction in force to pinch closed the hose by concentrating the force over a smaller area of the hose. The configuration of the blade tips and using two of them in opposition, as described above, further assist in lowering the necessary pinch force. The use of opposing blade tips is effective whether used in hinged, circular arc button embodiments or in linearly mounted embodiments. Another advantage of using two opposing blades is that it is a forgiving configuration if the blades somehow become misaligned. If misalignment occurs, the valve created by the blades will still function, albeit by a different mechanism. Typically, a misaligned valve will operate in a shear-pinch mode, however if the misalignment is substantial then a "blade on flat" mode may occur.

In addition to the configuration of the buttons and blade tips, the hoses themselves can be configured to reduce the necessary pinching force of the tool. The thicknesses of the hoses can be reduced to the minimum required, for example to avoid collapse in the suction hose 42. In addition, the hoses having a reduced hardness can be used in order to lower the pinching force. However, the hardness must stay above certain thresholds for the flush/irrigation hoses 46, 60 to maintain a certain burst strength and in the suction hose 42 to avoid collapse. One example of a suitable material for the hoses is silicone, although other materials may be used as well. In another embodiment, pinching force may also be reduced by providing one or more of the hoses with a pinching portion (not shown) in which the wall thickness of the hose is reduced in the portion of the hose to be pinched. To avoid collapse in the suction hose 42, the portions of the hose adjacent to the pinching portion may be strengthened, either by making them thicker or by any other suitable method known in the art.

Reducing the pinching force necessary to close the hoses further allows for valves that do not require additional mechanical advantage to fully actuate, which allows the components of the tool 10 to be assembled in a smaller, more compact housing 12. In addition, at least some embodiments combine the opening of one hose and the pinching of another hose into one operation performed by a single button. For example, the flush button 22 may, when actuated, overcome the spring bias holding the flush valve 88 in a closed position, thereby moving it to an open position, and simultaneously move the suction valve 98 into a closed position by causing it to be pinched by the second projection blade tip 90 and the suction hose blade tip 96.

In some embodiments of the dual and/or single cannula tool 10, it is desirable to tailor the force necessary to actuate the flush button 22 and/or the irrigation button 24. To accomplish this, a snapover member 118 may be included on the button and a snap projection 120 may extend from the housing 12, as shown in FIGS. 8, 16, and 17. These Figures show the snapover member 118 as part of the flush button 22; however the snapover member 118 may be incorporated into the irrigation button 24, as well. In at least one embodiment, the snapover member 118 extends from one of the button projections and has a curved tip 122 for engaging the snap projection 120. The snap projection 120 has a contact surface 124 which engages the curved tip 122, the contact surface 124 having a cam profile 126. The cam profile 126 can be tailored to provide a desired force profile as the button is actuated.

Without the snapover member 118, the force required to actuate the button is proportional to the spring constant with a small deflection requiring less force than full deflection. If it is desired to make the force profile such that more force is required at the beginning of actuation than at the end, a cam profile 126 such as that shown in FIGS. 15 and 16 may be used. As the button is depressed, the snapover member 118 must deflect as it slides across the contact surface 124. Accordingly, requiring a higher amount of deflection in the beginning will require a higher amount of force to begin actuation. However, once actuation is complete, the deflection is minimal and the force required to maintain the button in the actuated state is approximately equal to the force to compress the spring plus the force required to close any normally open hose(s) (e.g. the suction hose 42 in FIG. 15). This relatively low force at the end of actuation may be beneficial during periods of long actuation, for example during a lengthy operation, because it requires less strength to maintain actuation. Incorporating the snapover member 118 and snap projection 120 may be further advantageous if, for example, accidental actuation of a certain button is undesirable. It may also provide a more satisfactory tactile feel to the user of the tool 10.

The cam profile 126 can be tailored to provide a wide variety of force profiles in addition to the one described above. Another example is a cam profile that results in a constant force required to depress the button throughout its entire actuation. The force required to depress the button is the sum of the spring force and the snapover force at each given deflection, minus the force of the hose(s) acting on the button as it tries to return to its natural, open state. For the flush button 22, there is an additional required force of pinching closed the suction hose 42. Using this equation, other cam profiles can be designed for any desired force profile of the buttons.

Figure 18:
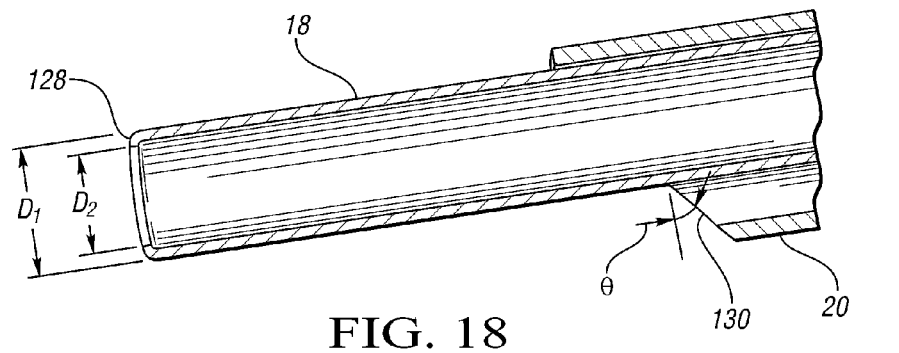
FIG. 18 is a side section view of an embodiment having dual cannulas in which the suction cannula has a tip with reduced diameter and the irrigation cannula is shorter than the suction cannula and has an angled tip.

Additional features may be incorporated in to any of the embodiments discussed above in order to increase the effectiveness of the tool 10. To reduce the possibility of clogging, the suction cannula 18 may have a tip 128 having a reduced diameter $D_2$ compared to the outer diameter $D_1$ of the rest of the cannula 18, such as shown in FIG. 18. The reduced tip diameter $D_2$ only allows debris having a diameter smaller than the cannula 18 diameter $D_1$ to enter, reducing the likelihood of clogging once inside. In at least one embodiment having a dual cannula, such as shown in FIG. 18, the irrigation cannula 20 may have a shorter length than the suction cannula 18. The irrigation cannula 20 may also have an angled tip 130, such that it has a shorter length at its farthest point from the suction cannula 18. In at least one embodiment, the angle θ of the tip is from 20 to 70 degrees. In another embodiment, the angle is from 30-60 degrees. In another embodiment, the angle is from 40-50 degrees.

Figure 19:
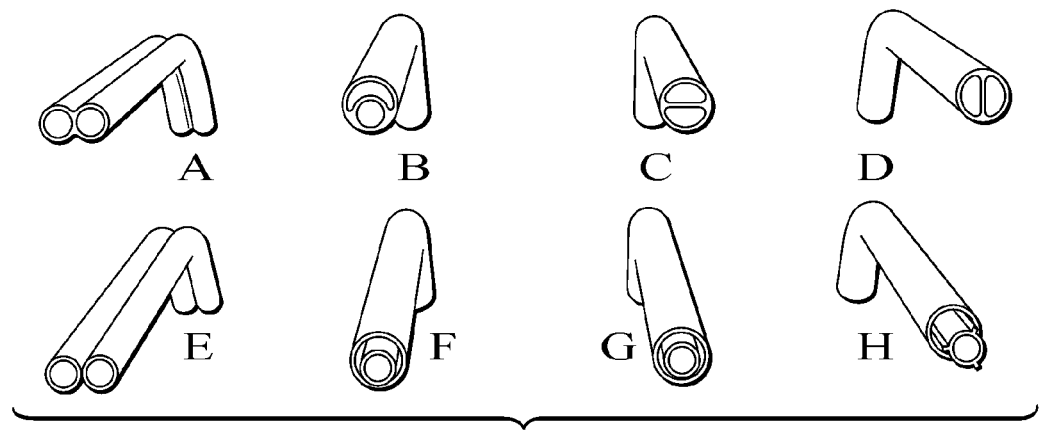
FIGS. 19A-19H are perspective views of various embodiments of dual cannula configurations.

In dual cannula embodiments, the shape and configuration of the cannulas is not limited to separate cannulas stacked vertically, such as shown in FIGS. 1 and 3. The suction cannula 18 and irrigation cannula 20 may be formed as one piece but divided to have separate lumens, such as shown in FIGS. 19A-D. Alternatively, they may be formed as independent and horizontally adjacent, such as shown in FIG. 19E. In other embodiments, they may be coaxial, such as shown in FIGS. 19F-H. In coaxial embodiments, the irrigation cannula 20 is typically (but not necessarily) the outer, shorter cannula.

Figure 20:
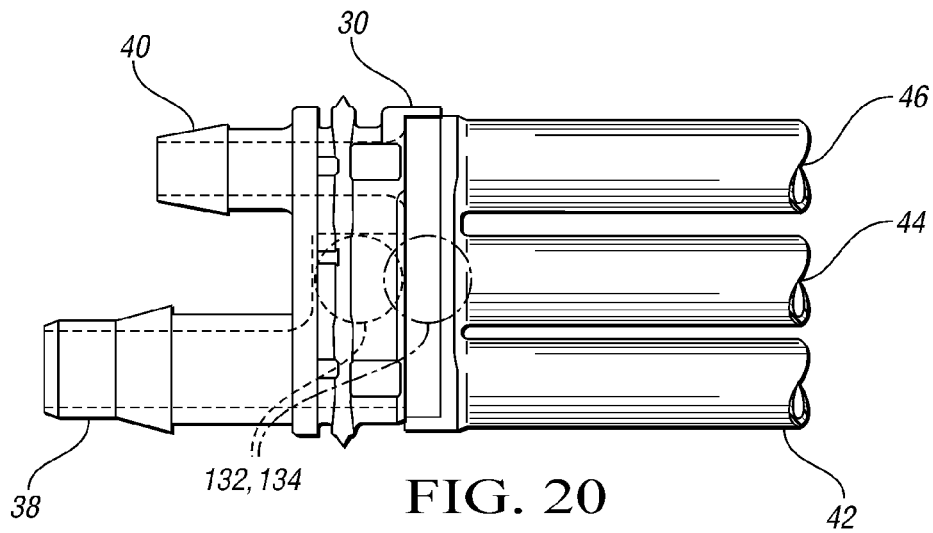
FIG. 20 is a phantom view of an embodiment of a ball check valve disposed in the rear manifold.
Figure 21:
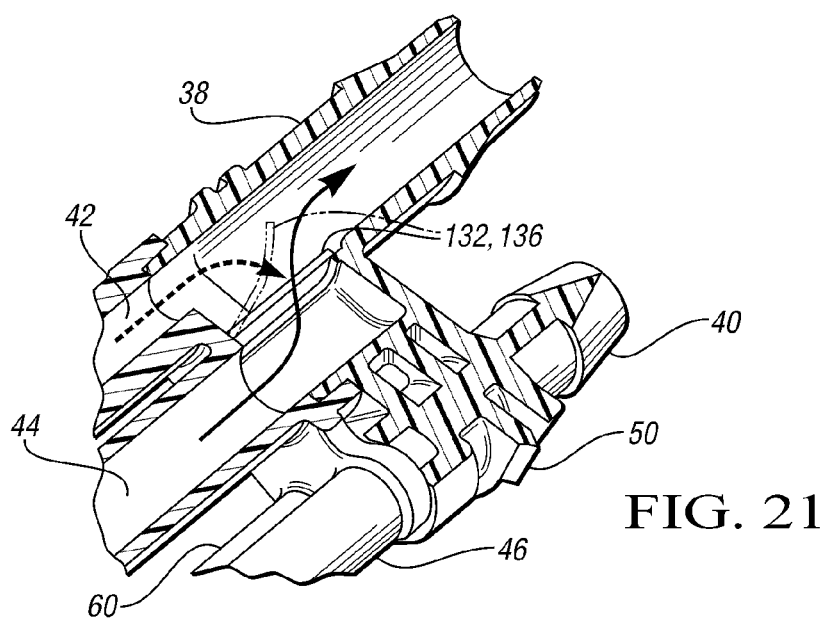
FIG. 21 is a sectioned perspective view of an embodiment of a reed check valve disposed in the rear manifold.

With respect to FIGS. 20 and 21, in some embodiments a check valve 132 may be provided at either end of the control port hose 44 or within the control port hose to allow air to be pulled into and through the control port hose 44 but prevent any fluid from exiting therefrom. For example, the check valve 132 may be located in the rear manifold 30, within the control port hose 44 (i.e. an in-line valve), or near the open port 52 (e.g. attached to the irrigation button 24 in some dual cannula embodiments). The check valve 132, for example a one-way valve, may prevent flush fluid from exiting through the control port hose 44 and out the open port 52 in the event that a clog occurs in the external suction supply line (not shown). If such a clog were to occur, then without a check valve 132 it may be possible during a partial pressure flush (described above) for flush water to travel past the suction valve 98 and back up into the control port hose 44, eventually exiting through the open port 52.

In at least one embodiment, an example of which is shown in FIG. 20, the check valve 132 is a ball check valve 134. In the embodiment shown, the ball check valve 134 is located at least partially within the rear manifold 30. The ball check valve 134 works by moving towards the proximal end of the tool 10 when suction is being applied, leaving a gap for the air to pass, and moving distally to seal the control port hose 44 when fluid tries to enter the control port hose from the proximal end. The ball check valve 134 is not limited to being located within the rear manifold, for example it may be located at the distal end of the control port hose 44. In at least one embodiment, however, the ball check valve 134 is located at least partially within the rear manifold 30 such that if a small amount of fluid leaks through the valve, there is a section of the control port hose 44 to hold the fluid and it will not exit the tool 10.

In other embodiments, an example of which is shown in FIG. 21, the check valve 132 is a reed valve 136. In the embodiment shown, the reed valve 136 is located at least partially within the rear manifold 30. The reed valve 136 works by flexing outward when suction is being applied, leaving a gap for the air to pass, and returning to a closed position to seal the control port hose 44 when fluid tries to enter the control port hose from the proximal end. The reed valve 136 is not limited to being located within the rear manifold, for example it may be located at the distal end of the control port hose 44. In at least one embodiment, however, the reed valve 136 is located at least partially within the rear manifold 30 such that if a small amount of fluid leaks through the valve, there is a section of the control port hose 44 to hold the fluid and it will not exit the tool 10.

While the illustrated embodiments show ball check valves and reed valves, any suitable check valve may be used to allow air to be suctioned into the tool 10 through the control port hose 44 while preventing fluid from escaping the tool 10 therefrom. Other examples (not shown) of possible check valves include in-line valves, umbrella valves, and slit/duckbill valves. These valves may be positioned within the control port hose 44, at either end of the control port hose 44, or any other suitable location to perform the desired function.

In at least one embodiment, the tool 10 may be configured to be disposable such that it may be used once or several times and then replaced. The tool 10 may be provided with supply lines (not shown) that extend between the suction terminal 38 and the source of suction and the irrigation terminal 40 and the source of irrigation. In one embodiment, the supply lines are PVC tubing, however any suitable material may be used. In one embodiment, the irrigation supply line may be connected to an IV bag having a pressure cuff.

In other embodiments, a pump or compressed air may be used to increase the pressure and/or volume flow through the supply line and the flush hose 46 and/or irrigation hose 60. Any suitable type of pump may be used, for example a peristaltic pump. In embodiments where a peristaltic pump is used, the supply lines (if provided with the tool 10) may be used with the peristaltic pump directly. The use of peristaltic pumps may be advantageous since they are generally available in hospitals for procedures such as dialysis and infusion. In embodiments where there is increased pressure in the supply lines, a flow controlling valve or a flow limiting orifice may be provided in one or both of the flush hose 46 and the irrigation hose 60 in order to reduce the pressure or the volume flow therethrough.

In at least some embodiments described above, there is at least one "normally closed" hose when no buttons are actuated. Depending on the materials used and the conditions during storage and shipping, it may be possible for the hoses to take on a permanent or semi-permanent set in the closed position such that they do not fully open when the buttons are actuated. For example, hoses made of rubber may set in elevated temperatures. To mitigate or eliminate this potential issue, the tool 10 may be packaged such that buttons that are configured to open the normally closed hoses are in an at least partially actuated position, thereby not allowing them to stay in a fully closed position for long periods of time. This may be accomplished using any suitable method known in the art, for example using a pull-pin or a shrink sleeve.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A handheld tool for providing irrigation and suction, the tool comprising:
    a housing, the housing having defined therein an open port in fluid communication with an outside atmosphere;
    a suction terminal configured to connect to a source of suction and an irrigation terminal configured to connect to a source of irrigation fluid;
    a cannula extending from a distal end of the housing configured to deliver fluid or remove fluid or debris from a body site;
    a suction hose coupled at one end to the suction terminal and extending to and coupled to a proximal end of the cannula;
    a control port hose in fluid communication with the suction terminal at one end and the open port at another end;
    a flush hose coupled at one end to the irrigation terminal and at the other end to the suction hose; and
    a flush button disposed within the housing;
    wherein the suction hose is configured to be normally open and the flush hose is configured to be normally closed and actuation of the flush button causes the flush hose to switch to an open position, allowing fluid to flow to the cannula, and switches the suction hose into a closed position, such that fluid or debris do not travel to the suction source; and
    wherein a partial actuation of the flush button causes the suction hose and the flush hose to be in a partially open position, thereby allowing a reduced amount of fluid, compared to a full actuation, to flow through the flush channel, a portion of which will flow to the cannula and a portion of which will flow to the suction source.

2. The tool of claim 1, wherein a front manifold and a rear manifold are disposed within the housing, the rear manifold comprising the suction terminal and the irrigation terminal;
    the cannula extends from a distal end of the front manifold;
    the suction hose extends from the suction terminal of the rear manifold to a suction channel in a proximal end of the front manifold, the suction channel in fluid communication with the cannula;
    the control port hose extends from the suction terminal of the rear manifold to the open port; and the flush hose extends from the irrigation terminal of the rear manifold to a flush channel in the proximal end of the front manifold, the flush channel terminating in the suction channel.

3. The tool of claim 2, wherein the cannula is a suction cannula and the tool further comprises an irrigation hose extending from the irrigation terminal of the rear manifold through a distal end of the housing and extending adjacent to the suction cannula to form an irrigation cannula; and an irrigation button disposed within the housing;

wherein the irrigation hose is configured to be normally closed and actuation of the irrigation button causes the irrigation hose to switch to an open position, allowing fluid to flow to the irrigation cannula.

4. The tool of claim 1, wherein the flush button further comprises:

a first projection configured to engage and pinch closed the flush hose in cooperation with a flush hose blade extending from the housing;

a second projection configured to engage and pinch closed the suction hose in cooperation with a suction hose blade extending from the housing; and a spring disposed between the first projection and the housing, the spring configured to bias the first projection into a closed position with the first projection and the flush hose blade pinching closed the flush hose;

wherein actuation of the flush button causes the spring bias to be overcome, thereby causing the flush hose to switch to the open position and the suction hose to be in the closed position.

5. The tool of claim 4, wherein the first projection has a blade tip extending transverse to a longitudinal direction of the flush hose and the flush hose blade has a blade tip extending transverse to the longitudinal direction of the flush hose; and the second projection has a blade tip extending transverse to a longitudinal direction of the suction hose and the suction hose blade has a blade tip extending transverse to the longitudinal direction of the suction hose;

wherein the first projection blade tip and the flush hose blade tip are configured to pinch closed the flush hose and the second projection blade tip and the suction hose blade tip are configured to pinch closed the suction hose.

6. The tool of claim 3, wherein the irrigation button further comprises:

a third projection configured to engage and pinch closed the irrigation hose in cooperation with an irrigation hose blade extending from the housing; and a spring disposed between the third projection and the housing, the spring configured to bias the third projection into a closed position with the third projection and the irrigation hose blade pinching closed the irrigation hose;

wherein actuation of the irrigation button causes the spring bias to be overcome, thereby causing the irrigation hose to switch to the open position.

7. The tool of claim 6, wherein the third projection has a blade tip extending transverse to a longitudinal direction of the irrigation hose and the irrigation hose blade has a blade tip extending transverse to the longitudinal direction of the irrigation hose;

wherein the third projection blade tip and the irrigation hose blade tip are configured to pinch closed the irrigation hose.

8. The tool of claim 5, wherein the flush button is hinge-mounted in the housing such that the first projection and second projection travel in a circular arc when the flush button is actuated.

9. The tool of claim 8, wherein when the first projection blade tip and the flush hose blade tip pinch the flush hose closed, a line bisecting the first projection blade tip and a line bisecting the flush hose blade tip are substantially collinear; and when the second projection blade tip and the suction hose blade tip pinch the suction hose closed, a line bisecting the second projection blade tip and a line bisecting the suction hose blade tip are substantially collinear.

10. The tool of claim 2, wherein the flush channel extends into and terminates in the suction channel.

11. The tool of claim 2, wherein the flush channel extends into and terminates in the suction channel at a reentrant or rearward angle.

12. The tool of claim 3, wherein the control port hose terminates in an open port defined in the irrigation button.

13. The tool of claim 3, further comprising a sleeve disposed around the suction cannula and the irrigation cannula.

14. The tool of claim 9, wherein when the flush hose is pinched closed, the first projection blade tip and the flush hose blade tip are separated by a distance no greater than two times a wall thickness of the flush hose; and when the suction hose is pinched closed, the second projection blade tip and the suction hose blade tip are separated by a distance no greater than two times a wall thickness of the suction hose.

15. The tool of claim 1, wherein the flush button further comprises a snapover member extending from the button and having a curved tip for engaging a snap projection extending from the housing, the snap projection having a contact surface with a cam profile;

wherein the contact surface cam profile is configured to adjust a force necessary to actuate the flush button.

16. The tool of claim 15, wherein the contact surface cam profile is configured such that actuation of the flush button requires a greater force at a beginning of the actuation than at an end of the actuation by causing the curved tip to deflect a greater amount at the beginning of the actuation compared to the end of the actuation.

17. The tool of claim 1, wherein the cannula has first diameter and a tip having a second diameter that is smaller than the first diameter.

18. The tool of claim 3, wherein the irrigation cannula has a length that is shorter than a length of the suction cannula.

19. The tool of claim 2, further comprising a check valve configured to allow air to be suctioned through the control port hose to the source of suction but prevent fluid from the suction hose from escaping through the open port at the end of the control port hose.

20. The tool of claim 19, wherein the check valve is formed as a ball check valve or a reed valve.

21. The tool of claim 20, wherein the check valve is located at least partially within the rear manifold.

22. A handheld tool for providing irrigation and suction, the tool comprising:

a housing;

a front manifold and a rear manifold disposed within the housing, the rear manifold having a suction terminal configured to connect to a source of suction and an irrigation terminal configured to connect to a source of irrigation fluid;

a suction cannula extending from a distal end of the front manifold configured to deliver fluid or remove fluid or debris from a body site;

a suction hose extending from the suction terminal of the rear manifold to a suction channel in a proximal end of the front manifold, the suction channel in fluid communication with the suction cannula;

a control port hose extending from the suction terminal of the rear manifold and having one end in fluid communication with an open port defined in the housing and in fluid communication with an outside atmosphere;

a flush hose extending from the irrigation terminal of the rear manifold to a flush channel in the proximal end of the front manifold, the flush channel terminating in the suction channel;

a flush button disposed within the housing;

an irrigation hose extending from the irrigation terminal of the rear manifold through a distal end of the housing and extending adjacent to the suction cannula to form an irrigation cannula; and an irrigation button disposed within the housing;

wherein the suction hose is configured to be normally open and the flush hose and irrigation hose are configured to be normally closed; actuation of the flush button causes the flush hose to switch to an open position, allowing fluid to flow to the suction cannula, and switches the suction hose into a closed position, such that fluid or debris do not travel to the suction source; and actuation of the irrigation button causes the irrigation hose to switch to an open position, allowing fluid to flow to the irrigation cannula.

23. The tool of claim 22, wherein the flush button further comprises:

a first projection configured to engage and pinch closed the flush hose in cooperation with a flush hose blade extending from the housing;

a second projection configured to engage and pinch closed the suction hose in cooperation with a suction hose blade extending from the housing; and a first spring disposed between the first projection and the housing, the first spring configured to bias the first projection into a closed position with the first projection and the flush hose blade pinching closed the flush hose;

wherein actuation of the flush button causes the first spring bias to be overcome, thereby causing the flush hose to switch to the open position and the suction hose to be in the closed position; and the irrigation button further comprises:

a third projection configured to engage and pinch closed the irrigation hose in cooperation with an irrigation hose blade extending from the housing; and a second spring disposed between the third projection and the housing, the spring configured to bias the third projection into a closed position with the third projection and the irrigation hose blade pinching closed the irrigation hose;

wherein actuation of the irrigation button causes the spring bias to be overcome, thereby causing the irrigation hose to switch to the open position.

24. The tool of claim 23, wherein the first projection has a blade tip extending transverse to a longitudinal direction of the flush hose and the flush hose blade has a blade tip extending transverse to the longitudinal direction of the flush hose; and the second projection has a blade tip extending transverse to a longitudinal direction of the suction hose and the suction hose blade has a blade tip extending transverse to the longitudinal direction of the suction hose; and the third projection has a blade tip extending transverse to a longitudinal direction of the irrigation hose and the irrigation hose blade has a blade tip extending transverse to the longitudinal direction of the irrigation hose;

wherein the first projection blade tip and the flush hose blade tip are configured to pinch closed the flush hose; the second projection blade tip and the suction hose blade tip are configured to pinch closed the suction hose; and the third projection blade tip and the irrigation hose blade tip are configured to pinch closed the irrigation hose.

25. The tool of claim 22, wherein the flush channel extends into and terminates in the suction channel at a reentrant or rearward angle.

26. A handheld tool for providing irrigation and suction, the tool comprising:

a housing;

a front manifold and a rear manifold disposed within the housing, the rear manifold having a suction terminal configured to connect to a source of suction and an irrigation terminal configured to connect to a source of irrigation fluid;

a cannula extending from a distal end of the front manifold configured to deliver fluid or remove fluid or debris from a body site;

a suction hose extending from the suction terminal of the rear manifold to a suction channel in a proximal end of the front manifold, the suction channel in fluid communication with the cannula;

a control port hose extending from the suction terminal of the rear manifold and having one end in fluid communication with an open port defined in the housing and in fluid communication with an outside atmosphere;

a flush hose extending from the irrigation terminal of the rear manifold to a flush channel in the proximal end of the front manifold, the flush channel terminating in the suction channel; and a flush button disposed within the housing;

wherein the suction hose is configured to be normally open and the flush hose is configured to be normally closed and actuation of the flush button causes the flush hose to switch to an open position, allowing fluid to flow to the cannula, and switches the suction hose into a closed position, such that fluid or debris do not travel to the suction source.

27. The tool of claim 26, wherein the suction hose, control port hose, and flush hose are all completely disposed within the housing and the flush button is hinge-mounted within the housing such that a non-hinged end of the button travels in a circular arc when actuated and causes a portion of the non-hinged end to pinch the suction hose into the closed position.

28. The tool of claim 27, wherein the flush button further comprises:

a first projection formed on the non-hinged end and having a blade tip extending transverse to a longitudinal direction of the flush hose configured to engage and pinch closed the flush hose in cooperation with a flush hose blade extending from the housing and having a blade tip extending transverse to the longitudinal direction of the flush hose;

a second projection having a blade tip extending transverse to a longitudinal direction of the suction hose configured to engage and pinch closed the suction hose in cooperation with a suction hose blade extending from the housing and having a blade tip extending transverse to the longitudinal direction of the suction hose; and a spring disposed between the first projection and the housing, the spring configured to bias the first projection into a closed position with the first projection blade tip and the flush hose blade tip pinching closed the flush hose;

wherein actuation of the flush button causes the spring bias to be overcome, thereby causing the flush hose to switch to the open position and the suction hose to be in the closed position with the second projection blade tip and the suction hose blade tip pinching closed the suction hose.

29. The tool of claim 28, wherein when the first projection blade tip and the flush hose blade tip pinch the flush hose closed, a line bisecting the first projection blade tip and a line bisecting the flush hose blade tip are substantially collinear; and when the second projection blade tip and the suction hose blade tip pinch the suction hose closed, a line bisecting the second projection blade tip and a line bisecting the suction hose blade tip are substantially collinear.

* * * * *